US012237079B2

(12) United States Patent
Fisher-Stawinski et al.

(10) Patent No.: US 12,237,079 B2
(45) Date of Patent: Feb. 25, 2025

(54) DYNAMIC GEOFENCING-ENABLED PHYSIOLOGICAL RISK MONITORING SYSTEM IN PHYSICAL AND MIXED REALITY ENVIRONMENTS

(71) Applicant: INTERNATIONAL BUSINESS MACHINES CORPORATION, Armonk, NY (US)

(72) Inventors: Steven Lee Fisher-Stawinski, Buffalo Grove, IL (US); Moitreyee Mukherjee-Roy, San Jose, CA (US); Scott E. Schneider, Rolesville, NC (US); Shikhar Kwatra, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 322 days.

(21) Appl. No.: 17/474,681

(22) Filed: Sep. 14, 2021

(65) Prior Publication Data
US 2023/0081225 A1 Mar. 16, 2023

(51) Int. Cl.
*G16H 40/63* (2018.01)
*G06F 3/01* (2006.01)
*G08B 21/02* (2006.01)

(52) U.S. Cl.
CPC .......... *G16H 40/63* (2018.01); *G06F 3/011* (2013.01); *G08B 21/0236* (2013.01)

(58) Field of Classification Search
None
See application file for complete search history.

(56) References Cited

U.S. PATENT DOCUMENTS 8,595,161 B2 11/2013 Bearman
9,075,909 B2 7/2015 Almogy
(Continued)

FOREIGN PATENT DOCUMENTS

CN 106781245 A 5/2017
CN 108025767 A 5/2018
(Continued)

OTHER PUBLICATIONS

Fozouni P, Son S et al. Amplification-free detection of SARS-CoV-2 with CRISPR-Cas 13a and mobile phone microscopy. Cell. Jan. 21, 2021;184(2):323-333.e9. doi: 10.1016/j.cell.2020.12.001. Epub Dec. 4, 2020. PMID: 33306959; PMCID: PMC7834310. (Year: 2020).*
(Continued)

*Primary Examiner* — Katherine Kolosowski-Gager
(74) *Attorney, Agent, or Firm* — Robert D. Bean

(57) ABSTRACT

According to one embodiment, a method, computer system, and computer program product for tracking positions and characteristics of one or more individuals in proximity to a user to dynamically assess a threat of physiological harm to the user is provided. The present invention may include identifying, by one or more sensors integrated into one or more wearable devices on the person of a user, one or more individuals in proximity to the user; generating a dynamic threshold corresponding to each of the one or more individuals; responsive to identifying one or more characteristics of the individual, updating the dynamic threshold; and responsive to a distance between an individual of the one or more individuals and the user falling below the dynamic threshold associated with the individual, transmitting an alert to the user.

20 Claims, 5 Drawing Sheets

(56) References Cited

U.S. PATENT DOCUMENTS

| | | | |
|---|---|---|---|
| 10,121,070 | B2 | 11/2018 | Derenne |
| 11,704,990 | B2* | 7/2023 | Levin ................... G08B 21/182 |
| | | | 340/686.6 |
| 2013/0085345 | A1 | 4/2013 | Geisner |
| 2017/0213079 | A1 | 7/2017 | Herger |
| 2020/0279339 | A1* | 9/2020 | Akutagawa ........ A61B 10/0064 |
| 2021/0027063 | A1 | 1/2021 | So |
| 2021/0058736 | A1 | 2/2021 | Ghazzaoui |
| 2021/0166803 | A1 | 6/2021 | Ellis |
| 2022/0102012 | A1* | 3/2022 | Son ........................ G16H 10/40 |
| 2022/0293278 | A1* | 9/2022 | Correnti ............... G06V 40/172 |
| 2023/0162396 | A1* | 5/2023 | German ................... G01S 5/16 |
| | | | 345/633 |

FOREIGN PATENT DOCUMENTS

| | | |
|---|---|---|
| CN | 111798646 A | 10/2020 |
| CN | 111816322 A | 10/2020 |
| KR | 20200145126 A | 12/2020 |
| WO | 2023040764 A1 | 3/2023 |

OTHER PUBLICATIONS

Fisher-Stawinski, et al., "Dynamic Geofencing-Enabled Physiological Risk Monitoring System in Physical and Mixed Reality Environments," Application and Drawings, Filed on Sep. 9, 2022, 49 Pages, Related PCT Patent Application Serial No. PCT/CN2022/118069.

International Searching Authority, "Notification of Transmittal of the International Search Report and the Written Opinion of the International Searching Authority, or Declaration," Patent Cooperation Treaty, Nov. 30, 2022, 9 pages, International Application No. PCT/CN2022/118069.

Anonymous, "Corona alert! New smartphone app may warn when you come in contact with Covid-19 patient," The Economic Times [e-paper], Apr. 17, 2020, 2 pages, Retrieved from the Internet: <URL: https://economictimes.indiatimes.com/magazines/panache/corona-alert-new-smartphone-app-may-warn-when-you-come-in-contact-with-covid-19-patient/articleshow/75200565.cms>.

Disclosed Anonymously, "Disclosed method is a solution for dynamically recommending preferred commodity based on profile," IP.com, Feb. 17, 2019, 6 pages, IP.com No. IPCOM000257490D, Retrieved from the Internet: <URL: https://priorart.ip.com/IPCOM/000257490>.

Disclosed Anonymously, "Three-Dimensional Map Routing to Minimize Pathogen Exposure During a Pandemic Based on Augmented Reality, Machine Learning, and Internet of Things," IP.com, Mar. 8, 2021, IP.com No. IPCOM000265171D, Retrieved from the Internet: <URL: https://priorart.ip.com/IPCOM/000265171>.

Ho, et al., "Social Distancing 2.0 with Privacy-Preserving Contact Tracing to Avoid a Second Wave of COVID-19," Social and Information Networks (cs.SI), Aug. 6, 2020, arXiv:2006.16611, Retrieved from the Internet: <URL: https://arxiv.org/abs/2006.16611>.

Mell, et al., "The NIST Definition of Cloud Computing", National Institute of Standards and Technology, Special Publication 800-145, Sep. 2011, 7 pages.

\* cited by examiner

DYNAMIC GEOFENCING-ENABLED PHYSIOLOGICAL RISK MONITORING SYSTEM IN PHYSICAL AND MIXED REALITY ENVIRONMENTS

BACKGROUND

The present invention relates, generally, to the field of computing, and more particularly to mixed reality.

Mixed reality is a field concerned with merging real and virtual worlds such that physical and digital objects co-exist and interact in real time. Mixed reality does not exclusively take place in either the physical or virtual worlds but is a hybrid of reality and virtual reality. As such, mixed reality describes everything in the reality-virtuality continuum except for the two extremes, namely purely physical environments and purely virtual environments. Accordingly, mixed reality includes augmented virtuality (AV), augmented reality (AR) and virtual reality (VR). Mixed reality has found practical applications in remote working, military and commercial training, games, and medicine, among others.

SUMMARY

According to one embodiment, a method, computer system, and computer program product for tracking positions and characteristics of one or more individuals in proximity to a user to dynamically assess a threat of physiological harm to the user is provided. The present invention may include identifying, by one or more sensors integrated into one or more wearable devices on the person of a user, one or more individuals in proximity to the user; generating a dynamic threshold corresponding to each of the one or more individuals; responsive to identifying one or more characteristics of the individual, updating the dynamic threshold; and
    responsive to a distance between an individual of the one or more individuals and the user falling below the dynamic threshold associated with the individual, transmitting an alert to the user.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
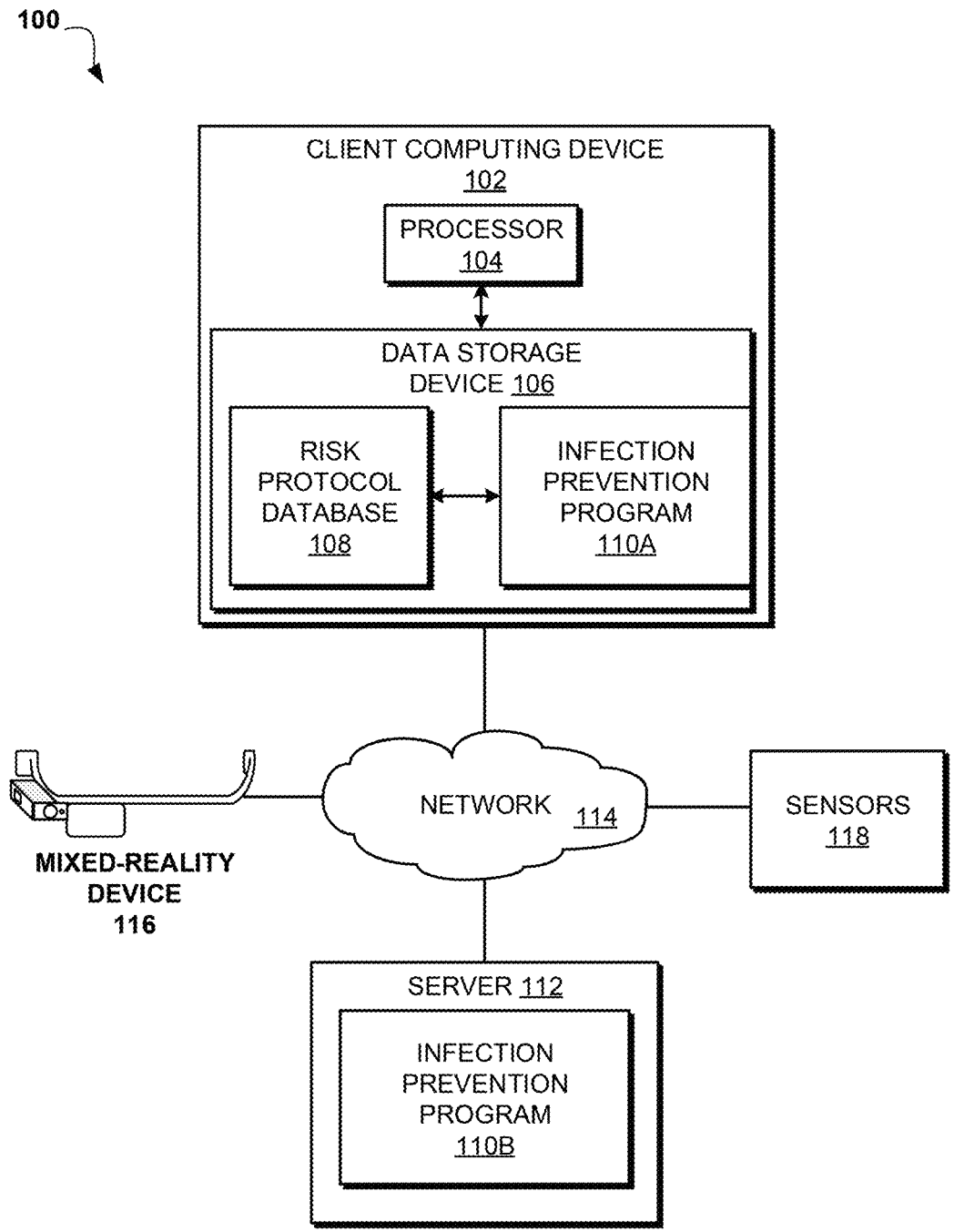
FIG. 1 illustrates an exemplary networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate to the field of computing, and more particularly to mixed reality. The following described exemplary embodiments provide a system, method, and program product to, among other things, detect, dynamically geofence, and warn a user of potential nearby physiological hazards based on a physiological risk profile tailored to the user, utilizing mixed-reality devices. Therefore, the present embodiment has the capacity to improve the technical field of mixed reality by enabling automatic real time detection of, and a dynamically tailored response to, physiological hazards identified in the proximity of the user, taking into account the unique vulnerabilities of the user.

As previously described, mixed reality is a field concerned with merging real and virtual worlds such that physical and digital objects co-exist and interact in real time. Mixed reality does not exclusively take place in either the physical or virtual worlds but is a hybrid of reality and virtual reality; as such, mixed reality describes everything in the reality-virtuality continuum except for the two extremes, namely purely physical environments and purely virtual environments. Accordingly, mixed reality includes augmented virtuality (AV), augmented reality (AR) and virtual reality (VR). Mixed reality has found practical applications in remote working, military and commercial training, games, and medicine, among others.

Society faces an ever-changing world of health and safety risks, with new risks and new knowledge regarding existing risks are discovered every day, ever-changing mitigation strategies, and incomplete compliance from members of the public. Keeping track of physiological risks, most effective mitigation strategies, and current legally mandated risk mitigation measures is difficult enough. Since staying at home is not an option for everyone, some individuals must venture into public spaces, and during such forays, knowing how to respond to nearby people who are partially complying or entirely failing to comply with legally mandated risk mitigation measures based on all of the aforementioned information is more difficult still. On top of this, many individuals have some number and variety of health conditions that render them particularly vulnerable to certain threats. Additionally, venturing into crowded public spaces can be unavoidable, and even an alert individual can fail to spot people nearby who might present significant physiological risks; human vision is limited in scope, and peripheral vision only goes so far. As such, it may be advantageous to, among other things, implement a system that identifies all individuals near a user, calculating a dynamic threshold distance from the user associated with each different individual and tailored based on risks presented by the individual and health risks of the user, and warns the user via mixed-reality graphical elements if an individual moves closer to the user than the dynamic threshold distance; such a system provides coverage in more directions than that achievable with the human eye, alerting the user to and protecting the user from threats that the user might not otherwise have perceived, unobtrusively alerting the user to risks, and providing up to date responses that best complement the user's own health needs, thereby providing the user with improved safety and protection even in chaotic, crowded public spaces.

According to at least one embodiment, the invention is a method of gathering proximity data, identifying the position and distance of one or more individuals within the proximity data, generating a dynamic threshold distance based on health characteristics or behavior characteristics of the individual, a protocol from a database of risk mitigation protocols, and/or a physiological risk profile of a user associated with the mixed reality device, and, responsive to the distance of an individual from the user decreasing below the dynamic threshold associated with that individual, alerting the user.

According to at least one embodiment of the invention, gathering proximity data may include collecting data from one or more sensors providing an arc of coverage around the user within which the sensors may identify individuals, and measure the position and range of those individuals. The sensors may further be capable of observing health characteristics or behavioral characteristics of the individual. The sensors may be in communication with or integrated into a mobile device worn or carried by the user, such as a mixed reality headset, smart watch, smart phone, et cetera. The sensors may be numbered and angled to provide a fixed arc of coverage, may be individually or collectively movable to provide dynamic coverage, and/or may be in motion fast enough to sweep an arc such that sensor coverage is provided at intervals regular and small enough to maintain constant, if intermittent, coverage of the arc. In some embodiments of the invention, the sensors may provide full 360-degree coverage around the user. The sensors may additionally provide vertical coverage, for example to detect individuals on balconies or otherwise on different elevations from the user. In some embodiments, the sensors may be either or a combination of visible light or infrared cameras, and may additionally comprise sensors capable of identifying health or behavioral characteristics such as lidar, microphones, laser rangefinders, et cetera.

According to at least one embodiment of the invention, health characteristics of an individual may be observable characteristics of the individual that indicate a health status of the individual and potential physiological risks linked to that health status. Such health characteristics may include whether the individual is coughing, sneezing, breathing heavily, perspiring, exhibiting a high heart rate, whether skin is flushed, pale, or jaundiced, et cetera. In some embodiments, for example where the mixed reality device is equipped with a ranged thermal sensor such as an infrared camera, health characteristics could include body temperature. In some embodiments of the invention, health characteristics may include vaccination status, health status, sickness warnings, et cetera transmitted by a mobile device associated with the individual.

According to at least one embodiment of the invention, behavioral characteristics of an individual may be observable characteristics or behaviors of the individual that may or may not have any connection with a health status of that individual, but which nevertheless may be used to assess a physiological risk to the user. For example, behavioral characteristics may include whether the individual is wearing a mask or otherwise visibly complying with risk mitigation protocols and/or legally mandated risk mitigation measures, exhibiting erratic or violent movements, et cetera. In some embodiments of the invention, additional behavioral characteristics may be added based on the physiological risk profile of the user. For example, if the physiological risk profile indicates that the user is epileptic, behavioral characteristics may include blinking lights on the person of the individual.

According to at least one embodiment of the invention, a risk mitigation protocol may be a series of instructions regarding measures that a user can take to reduce risk of injury, infection, illness, et cetera to the user and/or other individuals. Risk mitigation protocols may include keeping a minimum distance from other individuals, wearing protective equipment such as a mask or gloves, coughing away from other people, taking particular medication when exposed to certain conditions or behaviors, et cetera. Legally mandated risk mitigation measures may be a subset of risk mitigation protocols which the user is legally obligated to follow and comply with by order of a regulatory authority such as federal, state or local government. For example, during an infectious disease outbreak, public health officials may release a risk mitigation protocol advising individuals to avoid skin-to-skin contact, such as handshakes, with people showing symptoms, such as fever, and for individuals with elevated risk factors, such as high blood pressure, to wear surgical gloves in public. There may be multiple risk mitigation protocols pertaining to a single physiological risk, and such risk mitigation protocols may comprise instructions for reducing the risk in different contexts; for example, a first risk mitigation protocol for a infectious disease may be directed to steps for avoiding exposure to the disease, and a second risk mitigation protocol for the infections disease may be directed to steps for avoiding or mitigating infection after a potential exposure.

Risk mitigation protocols may be obtained from one or more repositories of risk mitigation protocols maintained by the government, private organizations, and/or individuals. In some embodiments of the invention, the system may generate and/or maintain a database of risk mitigation protocols selected, modified, and/or otherwise tailored to the physiological risk profile of the user, such that the risk mitigation database comprises all risk mitigation protocols that are of relevance to the user, for example associated with health conditions contained within the user's physiological risk profile.

According to at least one embodiment of the invention, a physiological risk profile of a user may be a profile associated with the user that documents health conditions of the user such as injuries, past and current illnesses, allergies, sensitivities, immune status, congenital abnormalities, physiological characteristics, whether the user is under the effects of certain medications or treatments, et cetera, and the ways in which these health conditions affect the user's vulnerability or resistance to any illnesses, behaviors, or conditions that the user may encounter that could ultimately result in physiological harm to the user. In some embodiments of the invention, the physiological risk profile of the user may include conditions or factors that affect the user's vulnerability or resistance to any illnesses, behaviors, or conditions but which aren't necessarily health conditions, such as whether the user is wearing protective gear such as masks or gloves, whether local environmental conditions such as wind or humidity favor or inhibit airborne transmission of diseases, et cetera.

According to at least one embodiment of the invention, the system may take into account any behavioral characteristics and health characteristics observed and/or detected in the individual based on the proximity data and identify one or more potential physiological risks which are associated with the observed behavioral characteristics and/or health characteristics. In some embodiments of the invention, the system may consult a database comprising a list of physiological risks, where each physiological risk is linked with a list of behavioral characteristics and/or health characteristics that are symptomatic of, statistically correspond with, increase the likelihood of, or are otherwise associated with the physiological risk. The system may search the database for the identified behavioral characteristics and health characteristics, and return all physiological risks associated with any of the detected characteristics.

In some embodiments of the invention, the system may calculate an individualized risk score associated with each of the physiological risks identified in connection with characteristics observed in an individual, based for example on the number of detected behavioral and/or health characteristics that correspond with the physiological risk. The individualized risk score may also be based on the nature of the physiological risk and factors that influence the likelihood and severity of harm to the user. In the example of diseases, these factors may include virulence, infectivity, transmissibility, fatality rate, recovery rate, reoccurrence rate, chances of rendering the user vulnerable to other physiological risks (by, for example, weakening the immune system), and possible long-term effects of the disease, as well as the number of individuals in the area of the user currently infected, hospitalized, estimated to be carrying the disease, et cetera. For example, where the physiological risk is a particularly virulent disease, the individualized risk score may be high even where only one related characteristic is detected, because the risk of harm to the user is so high in the event that they contract the disease. The individualized risk score may also be calculated based on the physiological risk profile of the user; the risk score may, for example, be greater for physiological risks that the user is particularly vulnerable to as a result of her health conditions or physiological traits and may be lesser for physiological risks to which the user is particularly resistant as a result of her health conditions and/or physiological traits.

According to at least one embodiments of the invention, the dynamic threshold may be a threshold measure of distance between the user and an identified individual. A dynamic threshold may be calculated for each of several or all individuals in proximity of the user. In calculating the dynamic threshold, the system may consult risk mitigation protocols associated with the physiological risks associated with the individual. In some embodiments of the invention, for example where multiple physiological risks are associated with an individual, and risk mitigation protocols associated with that plurality of physiological risks recommend maintaining safe distances of differing lengths from the individual, the system may select the longest safe distance to use as the dynamic threshold. The system may also select the distance recommended by the physiological risk mitigation profile associated with the physiological risk with the highest individualized risk score. The system may alternatively or additionally calculate a dynamic threshold distance that is proportional to the individualized risk score of the physiological risk with the highest individualized risk score or is proportional to the total risk score formed from adding individualized risk scores of all physiological risks associated with the individual. In some embodiments of the invention, the dynamic threshold distance may be adjusted or calculated based on historical successes and failures of the system to improve accuracy. The system may update the dynamic threshold by at least any of the above methods in real time or near-real-time, for as long as the individual is within tracking range of the sensors; the threshold distance may change as new characteristics are observed in the individual, and the potential danger posed by certain physiological risks associated with the individual change accordingly.

According to at least one embodiment of the invention, the system may erect a geofence around the user for each individual, where the radius of the geofence is the dynamic threshold distance associated with that individual. The geofence may be a virtual perimeter associated with an individual, centered on the user and extending out to the dynamic threshold distance associated with the individual. The geofence may move with the user such that the user as at the center of the geofence at all times, and may change in size as the dynamic threshold distance changes; all geofences may be visible to the user at all times in the form of graphical overlays within a mixed reality environment, may be individually toggleable by the user such that certain geofences or groups of geofences are visible, for example geofences corresponding to individuals associated with the highest individualized risk scores of any individual currently monitored by the system. In some embodiments of the invention geofences may be invisible to the user, or geofences may only be visible if the user indicates or selects an individual to whom the geofence is associated, for example using a gesture or eye tracking.

According to at least one embodiment of the invention, the system may constantly track the position and movement of identified individuals. If any individuals break the perimeter of their corresponding geofence, by moving within the threshold distance of the user, the system may alert the user to the intrusion; the system may alert the user through a text, graphical, and/or audio prompt, and may highlight the intruding individual in mixed reality graphical elements, and/or, if the intruding individual is behind or otherwise out of sight of the user, indicate to the user the direction and/or position of the intruding individual, such as via a virtual map or arrow overlaid onto the user's vision. In some embodiments of the invention, the system may additionally or alternatively present a recommended risk mitigation protocol to the user, where the recommended risk mitigation protocol may pertain to a context that matches that of the user (avoiding exposure to a disease, mitigating risk of disease after potential exposure, escaping belligerent individuals, et cetera). For example, if the intruding individual gets close enough to the user for potential exposure, the system may recommend that the user don protective gear, move in a particular direction, take a particular medication, et cetera.

In some embodiments of the invention, the system may determine a direction or escape course for the user to travel based on the location and movement of all tracked individuals in proximity to the user, such that the user's direction of travel carries the user out from within the dynamic threshold distance of the individual without entering into the dynamic threshold distance of any other tracked individuals. The system may communicate the determined escape course to the user through a virtual arrow or map overlaid onto the user's mixed reality environment.

According to at least one embodiment, the invention is a method of selecting a recommended risk mitigation protocol by, for one or more physiological risks, calculating a first individualized risk score for the user, where the individualized risk score represents a risk of the user experiencing the physiological condition; responsive to the first individualized risk score exceeding a threshold value, where the threshold value represents the highest acceptable level of risk, computing a second individualized risk score representing a risk of the user, where the second individualized risk score represents a risk of the user experiencing the physiological condition while following a risk mitigation protocol obtained from a repository of risk mitigation protocols. Responsive to the second individualized risk score being less than the first individualized risk score, selecting the risk mitigation protocol associated with the second individualized risk score.

In some embodiments of the invention, the system may calculate multiple second individualized risk scores, one for each of several risk mitigation protocols obtained from the repository of risk mitigation protocols. The system may compare the first individualized risk score against all or some subset of the second individualized risk scores and may select the risk mitigation protocol associated with a second individualized risk score that is lowest relative to the first individualized risk score. In some embodiments of the invention, the system may identify multiple risk mitigation protocols that are complimentary; in other words, a group of risk mitigation protocols which can be all be followed simultaneously without violating the tenets or instructions comprising any one of them. The system may, in such cases, calculate a single second risk mitigation protocol for a group of complimentary risk mitigation protocols, representing the risk of the user experiencing the physiological condition while following all or multiple of the group of complimentary risk mitigation protocols. In some embodiments of the invention, the system may transmit a recommendation to the user to follow the selected risk mitigation protocol.

According to at least one embodiment of the invention, the system may, by communicating with mobile devices of individuals in proximity to the user, identify individuals or groups of individuals that are following or have been recommended similar or compatible risk mitigation protocols. In some embodiments of the invention, the system may query nearby mobile devices for risk mitigation protocols that the user is following, based for example on prompting the user to enter risk mitigation protocols that the user is following. The system may query a nearby mobile device for risk mitigation protocols that a second user, or user of the nearby mobile device, has been recommended. If the query returns risk mitigation protocols that match those that the user is indicated to be following or has been recommended, the system may flag the second user, and/or individuals recorded as associated with the second user and following the same protocols as the second user, as "safe." Safe users may be indicated or highlighted via graphical elements within the mixed reality environment of the user. In some embodiments of the invention, the system may reassess the individualized risk scores associated with safe individuals based on the risk mitigation protocols that the safe individuals are following, and/or may adjust the dynamic threshold based on the reassessed individualized risk scores and risk mitigation protocols. The system may further select and recommend different risk mitigation protocols in the event of an intruding safe individual, based on the reassessed individualized risk scores. In some embodiments of the invention, the system may analyze behavioral characteristics of the safe users to verify that the safe users are actually following the instructions within the risk mitigation protocols.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to detect, dynamically geofence, and warn a user of potential nearby physiological hazards.

Referring to FIG. 1, an exemplary networked computer environment 100 is depicted, according to at least one embodiment. The networked computer environment 100 may include client computing device 102 and a server 112 interconnected via a communication network 114. According to at least one implementation, the networked computer environment 100 may include a plurality of client computing devices 102, risk protocol databases 108, sensors 118, and servers 112, of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements. For example, network 114 may comprise a plurality of discrete and separate communications channels, such that, for example, sensors 118 and mixed-reality device 116 communicate with client computing device 102, and/or infection prevention program 110A independently of each other.

Client computing device 102 may include a processor 104 and a data storage device 106 that is enabled to host and run a risk protocol database 108 and an infection prevention program 110A and communicate with the server 112 via the communication network 114, in accordance with one embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 4, the client computing device 102 may include internal components 402a and external components 404a, respectively.

The server computer 112 may be a laptop computer, netbook computer, personal computer (PC), a desktop computer, or any programmable electronic device or any network of programmable electronic devices capable of hosting and running an infection prevention program 110B and a database 116 and communicating with the client computing device 102 via the communication network 114, in accordance with embodiments of the invention. As will be discussed with reference to FIG. 4, the server computer 112 may include internal components 402b and external components 404b, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

Risk protocol database 108 may be one or more repositories of risk mitigation protocols maintained by the government, private organizations, and/or groups or individuals. In some embodiments of the invention, the infection prevention program 110A, 110B may generate and/or maintain one or more risk protocol databases 108, which may comprise risk mitigation protocols selected, modified, and/or otherwise tailored to the physiological risk profile of the user, such that the risk protocol database 108 comprises all risk mitigation protocols that are of relevance to the user, for example associated with health conditions contained within the user's physiological risk profile.

Mixed-reality device 116 may be any device which allows a user to perceive a mixed reality environment; accordingly, the mixed reality device 116 may be any device equipped with a display that can render a virtual environment, and hardware or software that enables the device to track its location and motion relative to the physical world, and by extension relative to virtual objects mapped to locations in the physical world. The mixed reality device 116 may be a general-purpose device owned by the user, such as a cell phone, or may be customized or specialized for an individual mixed reality experience or class of mixed reality experiences. Mixed reality device 116 may include such devices as VR headsets, AR headsets, smart glasses, tablets, mobile phones, et cetera. The user may wear or utilize mixed reality device 116 while experiencing the mixed reality environment. Mixed reality device 116 may be enabled to communicate with infection prevention program 110A, 110B residing within client computing device 102 and/or server 112 via the communication network 114, in accordance with one embodiment of the invention. In some embodiments of the invention, mixed-reality device 116 may be integrated with or comprise client computing device 102 and may be integrated with or in communication with sensors 118.

Sensors 118 may be one or more sensors configured to provide an arc of coverage around the user; within this arc, the sensors 118 may be capable of gathering data on all potentially human objects or all objects verified to be individuals, within the proximity of the user, where the proximity may be the maximum distance at which the infection prevention program 110A, 110B can identify, or can reliably identify, individuals within the data recorded by the sensors 118. The proximity may therefore be based on the accuracy with which infection prevention program 110A, 110B can identify individuals within the sensor data, and may be based on the quality of the sensor data and the power/sophistication of sensors 118. In some embodiments of the invention, proximity may be, at minimum, greater than a six-foot radius around the user. The sensors 118 may be in communication with or integrated into a mobile device worn or carried by the user, such as a mixed reality device 116, smart watch, smart phone, et cetera. The sensors 118 may be numbered and angled to provide a fixed arc of coverage, may be individually or collectively movable to provide dynamic coverage, and/or may be in motion fast enough to sweep an arc such that sensor coverage is provided at intervals regular and small enough to maintain constant, if intermittent, coverage of the arc. In some embodiments of the invention, the sensors 118 may provide full 360-degree coverage in a plane around the user. The sensors 118 may additionally provide a second dimension of coverage in the form of vertical coverage, for example to detect individuals on balconies or otherwise on different elevations from the user. In some embodiments, the sensors 118 may be either, or a combination of, visible light or infrared cameras, and may additionally comprise devices capable of identifying health or behavioral characteristics such as lidar, microphones, laser rangefinders, et cetera. The sensors 118 may be in communication with infection prevention program 110A, 110B, and may be integrated into client computing device 102, mixed-reality device 116, and/or may be deployed in the environment of the user.

According to the present embodiment, the infection prevention program 110A, 110B may be a program capable of detect, dynamically geofence, and warn a user of potential nearby physiological hazards. The infection prevention program 110A, 110B may be located on client computing device 102 or server 112 or on any other device located within network 114. Furthermore, infection prevention program 110A, 110B may be distributed in its operation over multiple devices, such as client computing device 102 and server 112. The infection prevention method is explained in further detail below with respect to FIG. 2.

Figure 2:
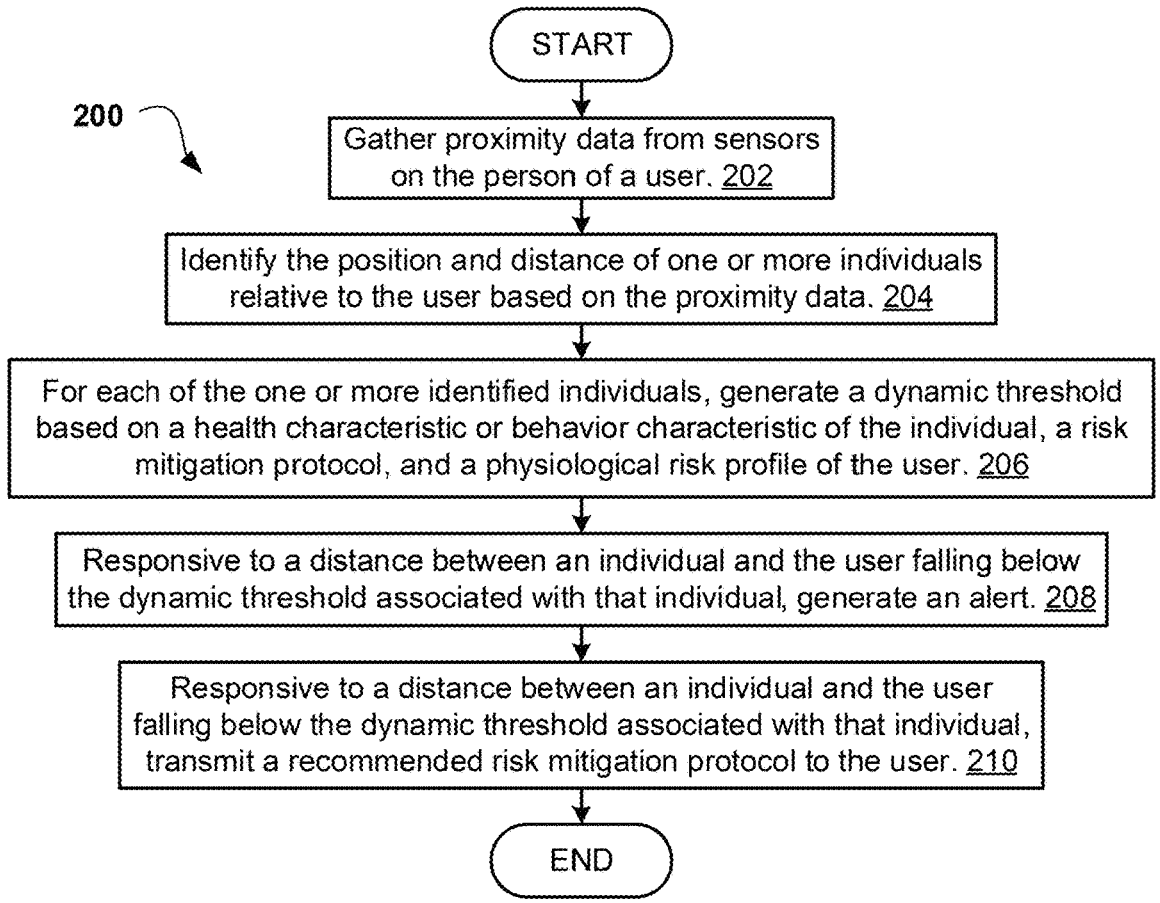
FIG. 2 is an operational flowchart illustrating an infection prevention process according to at least one embodiment.

Referring now to FIG. 2, an operational flowchart illustrating an infection prevention process 200 is depicted according to at least one embodiment. At 202, the infection prevention program 110A, 110B gathers proximity data from sensors 118 on the person of the user. Proximity data may be data gathered by a number of sensors 118 in real time or near real time within a full or partial arc around the user and proximate to the user, and may comprise sensor data about objects within the proximity of the user, including movement and position of objects, and any data on the objects that can be used to identify behavioral or health characteristics of objects determined to be individuals, such as visual data on the objects such as from cameras, thermal data such as from infrared cameras, et cetera. The arc of coverage within which sensors 118 collect proximity data may be fixed or dynamic, and may, for example, change to encompass areas where the user is not looking, or rotate continuously to provide near-constant sensor coverage in a full arc around the user. In some embodiments of the invention, proximity data may be collected by sensors 118 that are deployed in the environment of the user.

At 204, the infection prevention program 110A, 110B identifies the position and distance of one or more individuals relative to the user based on the proximity data. Here, the infection prevention program 110A, 110B may analyze objects within the proximity data using object recognition and image processing techniques, such as facial detection, moving object detection, outline of object recognition, et cetera to identify all humans within the proximity data. Once identified as humans, or individuals, infection prevention program 110A, 110B determines the position and distance of the identified individuals relative to the user based on laser rangefinding, lidar, sonar, stereoscopic ranging techniques, motion detection, and/or any other motion tracking or ranging techniques.

At 206, for each of the one or more individuals, the infection prevention program 110A, 110B generates a dynamic threshold distance based on a health characteristic or behavior characteristic of the individual, a risk mitigation protocol, and a physiological risk profile of the user. Characteristics may be observable characteristics of an individual that indicate potential physiological risks that the individual may pose to the user. Characteristics may include health characteristics, which may be traits or behaviors of an individual that indicate a health status of the individual and potential physiological risks linked to that health status. Characteristics may also include behavioral characteristics, which are traits or behaviors of the individual that may or may not have any connection with a health status of that individual, but which nevertheless may be used to assess a physiological risk to the user.

A risk mitigation protocol may be a series of instructions regarding measures that a user can take to reduce risk of injury, infection, illness, et cetera to the user and/or other individuals. Risk mitigation protocols may include keeping a minimum distance from other individuals, wearing protective equipment such as a mask or gloves, coughing away from other people, taking particular medication when exposed to certain conditions or behaviors, et cetera. Legally mandated risk mitigation measures may be a subset of risk mitigation protocols which the user is legally obligated to follow and comply with by order of a regulatory authority such as federal, state or local government. There may be multiple risk mitigation protocols pertaining to a single physiological risk, and such risk mitigation protocols may comprise instructions for reducing the risk in different associated contexts; for example, a first risk mitigation protocol for a infectious disease may be directed to steps for avoiding exposure to the disease, and a second risk mitigation protocol for the infections disease may be directed to steps for avoiding or mitigating infection after a potential exposure.

According to at least one embodiment of the invention, a physiological risk profile of a user may be a profile associated with the user that documents health conditions and physiological traits of the user that may inform the likelihood or severity of harm that any given physiological risk could inflict, such as injuries, past and current illnesses, allergies, sensitivities, immune status, congenital abnormalities, physiological characteristics, whether the user is under the effects of certain medications or treatments, et cetera.

The infection prevention program 110A, 110B may analyze proximity data corresponding to each or a subset of detected individuals using object detection, gesture recognition, et cetera to identify any behavioral characteristics and health characteristics of the individual, for instance by matching detected movements, gestures, objects, physiological traits, et cetera against known behaviors, articles of clothing, medical symptoms or conditions, et cetera, to produce a list of characteristics associated with the individual. The infection prevention program 110A, 110B may conduct this analysis in real time or at regular intervals, such that the infection prevention program 110A, 110B may continue to identify new characteristics of each individual to develop and continually maintain an accurate picture of the individual's characteristics. The infection prevention program 110A, 110B may analyze all detected individuals in parallel and/or may quickly switch between analyses of each individual. The infection prevention program 110A, 110B may consult a database comprising a list of physiological risks, where each physiological risk is linked with a list of characteristics that are symptomatic of, statistically correspond with, increase the likelihood of, or are otherwise associated with the physiological risk. The infection prevention program 110A, 110B may search the database for the identified behavioral characteristics and health characteristics, and return all physiological risks associated with any of the detected characteristics.

In some embodiments of the invention, the infection prevention program 110A, 110B may calculate an individualized risk score associated with each of the physiological risks identified in connection with characteristics observed in an individual, where the individualized risk score represents the overall likelihood that a given physiological risk will harm the user. The infection prevention program 110A, 110B may calculate the individualized risk score by assigning a weight based on the number of detected behavioral and/or health characteristics that correspond with the physiological risk, for at least the reason that the more characteristics associated with a physiological risk expressed by the individual, the greater the likelihood that the individual may expose the user to a disease or infect the user with a disease, hurt or damage the user through aggressive or wild behavior, et cetera. The infection prevention program 110A, 110B may also calculate the individualized risk score by assigning a weight to the physiological risk based on the nature of the physiological risk and related factors that influence the physiological risk's ability and likelihood to do harm to the user, such that more dangerous physiological risks are assigned higher weights and less dangerous physiological risks are assigned lower weights. The infection prevention program 110A, 110B may also calculate the individualized risk score by adjusting the weight of the physiological risk based on the physiological risk profile of the user, such that the weight of the physiological risk takes into account the vulnerabilities or resistances that the user might have to the physiological risk, such that the weight accurately reflects the user's contribution to the danger posed to the user by the physiological risk. The individualized risk score for a physiological risk may be the sum of the weights for the number of characteristics and/or the nature of the physiological risk as adjusted based on the user's physiological risk profile.

According to at least one embodiments of the invention, the dynamic threshold may be a threshold measure of distance between the user and an identified individual. The infection prevention program 110A, 110B may calculate a dynamic threshold for each of several or all individuals in proximity of the user. In calculating the dynamic threshold, the infection prevention program 110A, 110B may consult risk mitigation protocols associated with the physiological risks associated with the individual. In some embodiments of the invention, for example where multiple physiological risks are associated with an individual, and risk mitigation protocols associated with that plurality of physiological risks recommend maintaining safe distances of differing lengths from the individual, the infection prevention program 110A, 110B may select the longest safe distance to use as the dynamic threshold. The infection prevention program 110A, 110B may also select the distance recommended by the physiological risk mitigation profile associated with the physiological risk with the highest individualized risk score. The infection prevention program 110A, 110B may alternatively or additionally calculate a dynamic threshold distance that is proportional to the individualized risk score of the physiological risk with the highest individualized risk score, or is proportional to the total risk score formed from adding individualized risk scores of all physiological risks associated with the individual. In some embodiments of the invention, the dynamic threshold distance may be adjusted or calculated based on historical successes and failures of the infection prevention program 110A, 110B to improve accuracy. The infection prevention program 110A, 110B may update the dynamic threshold by at least any of the above methods in real time or near-real-time, for as long as the individual is within tracking range of the sensors; the threshold distance may change as new characteristics are observed in the individual, and the potential danger posed by certain physiological risks associated with the individual change accordingly.

According to at least one embodiment of the invention, the infection prevention program 110A, 110B may erect a geofence around the user for each individual, where the radius of the geofence is the dynamic threshold distance associated with that individual. The geofence may be a virtual perimeter associated with an individual, centered on the user and extending out to the dynamic threshold distance associated with the individual. The infection prevention program 110A, 110B may move the geofence with the user such that the user as at the center of the geofence at all times, and may change the size of the geofence as the dynamic threshold distance changes; the infection prevention program 110A, 110B may display all geofences to the user at all times in the form of graphical overlays within a mixed reality environment, may enable the user to individually toggle geofences such that certain geofences or groups of geofences are displayed, for example geofences corresponding to individuals associated with the highest individualized risk scores of any individual currently monitored by the infection prevention program 110A, 110B. In some embodiments of the invention geofences may be tracked by infection prevention program 110A, 110B but not displayed to the user, or infection prevention program 110A, 110B may only display geofences if the user indicates or selects an individual to whom the geofence is associated, for example using a gesture or eye tracking.

At 208, responsive to a distance between an individual and the user falling below the dynamic threshold associated with that individual, the infection prevention program 110A, 110B generates an alert. The infection prevention program 110A, 110B may constantly track the position and movement of identified individuals that remain within the proximity of the user. The infection prevention program 110A, 110B may detect when an individual has broken the perimeter of their corresponding geofence, by determining that the individual has moved within the dynamic threshold distance of the user. Upon detecting that an individual has entered the geofence, the infection prevention program 110A, 110B may alert the user to the intrusion; the infection prevention program 110A, 110B may alert the user through a text, graphical, and/or audio prompt, and may highlight the intruding individual in mixed reality graphical elements, and/or, if the intruding individual is behind or otherwise out of sight of the user, indicate to the user the direction and/or position of the intruding individual, such as via a virtual map or arrow overlaid onto the user's vision. In some embodiments of the invention, the infection prevention program 110A, 110B may additionally or alternatively present a recommended risk mitigation protocol to the user, where the recommended risk mitigation protocol may pertain to a context that matches that of the user (avoiding exposure to a disease, mitigating risk of disease after potential exposure, escaping belligerent individuals, et cetera). For example, if the intruding individual gets close enough to the user for potential exposure, the infection prevention program 110A, 110B may recommend that the user don protective gear, move in a particular direction, take a particular medication, et cetera.

At 210, responsive to a distance between an individual and the user falling below the dynamic threshold associated with that individual, the infection prevention program 110A, 110B transmits a recommended risk mitigation protocol to the user. The infection prevention program 110A, 110B may constantly track the position and movement of identified individuals that remain within the proximity of the user. The infection prevention program 110A, 110B may detect when an individual has broken the perimeter of their corresponding geofence, by determining that the individual has moved within the dynamic threshold distance of the user. The infection prevention program 110A, 110B may present a recommended risk mitigation protocol to the user, where the recommended risk mitigation protocol may pertain to a context that matches that of the user (avoiding exposure to a disease, mitigating risk of disease after potential exposure, escaping belligerent individuals, et cetera). For example, if the intruding individual gets close enough to the user for potential exposure, the infection prevention program 110A, 110B may recommend that the user don protective gear, move in a particular direction, take a particular medication, et cetera. An exemplary process for selecting a recommended risk mitigation protocol may be explained further with respect to FIG. 3.

Figure 3:
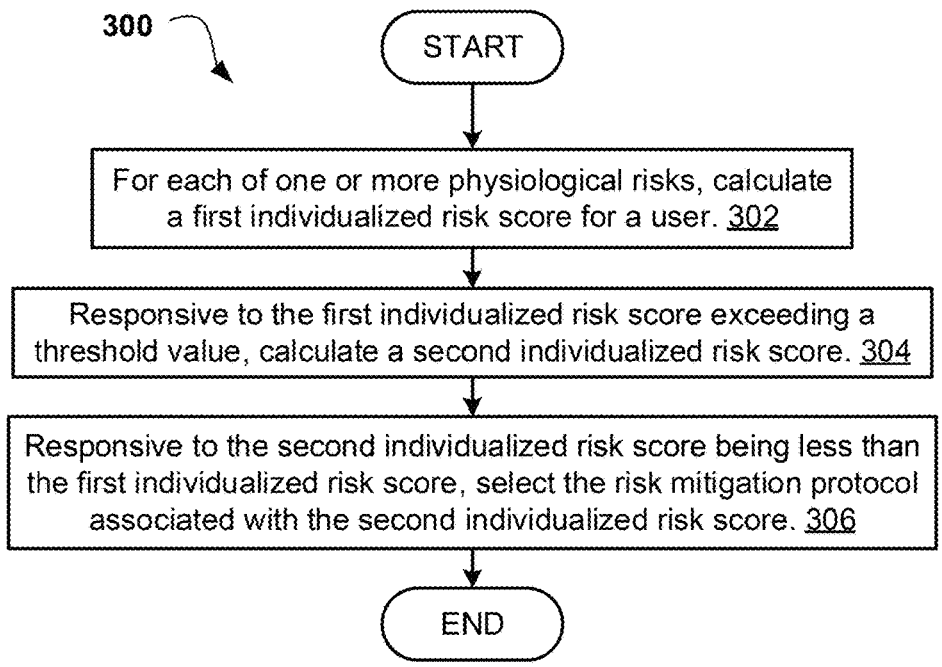
FIG. 3 is an operational flowchart illustrating an exemplary method for selecting recommended risk mitigation protocols in accordance with the infection prevention process, according to at least one embodiment.

With respect to FIG. 3, is an operational flowchart illustrating an exemplary method 300 for selecting recommended risk mitigation protocols in accordance with the infection prevention process is depicted, according to at least one embodiment. At 302, for each of one or more physiological risks, the infection prevention program 110A, 110B calculates a first individualized risk score for a user. The first individualized risk score represents the overall likelihood that a given physiological risk will harm the user, and infection prevention program 110A, 110B may calculate the first individualized risk score in substantially the same way as infection prevention program 110A, 110B calculates the individualized risk score. The physiological risks may be all physiological risks identified in connection with characteristics observed in an individual, based for example on the number of detected behavioral and/or health characteristics that correspond with the physiological risk.

At 304, responsive to the first individualized risk score exceeding a threshold value, infection prevention program 110A, 110B calculates a second individualized risk score. The threshold value represents the highest maximum level of risk that a user is willing to endure before seeking risk prevention measures. The threshold value may be based, for example, on user input, and/or may be based on a level of risk that has been found to statistically correlate with a spike in adverse health outcomes if exceeded, based on analysis of historical data. The second individualized risk score represents the overall likelihood that a given physiological risk will harm the user while the user is following a risk mitigation protocol obtained from a repository of risk mitigation protocols, and infection prevention program 110A, 110B may be calculate the second individualized risk score in substantially the same way as the first individualized risk score, except that the infection prevention program 110A, 110B adjusts the final value based on the projected effects of the risk mitigation protocol.

At 306, responsive to the second individualized risk score being less than the first individualized risk score, infection prevention program 110A, 110B selects the risk mitigation protocol associated with the second individualized risk score. In other words, upon determining that the risk mitigation protocol is projected to decrease the likelihood that the physiological risk will harm the user, the infection prevention program 110A, 110B selects the risk mitigation protocol for recommendation to the user. In some embodiments of the invention, the infection prevention program 110A, 110B may transmit the selected risk mitigation protocol to the user to follow the selected risk mitigation protocol.

In some embodiments of the invention, the infection prevention program 110A, 110B may calculate multiple second individualized risk scores, one for each of several risk mitigation protocols obtained from the repository of risk mitigation protocols. The infection prevention program 110A, 110B may compare the first individualized risk score against all or some subset of the second individualized risk scores and may select the risk mitigation protocol associated with a second individualized risk score that is lowest relative to the first individualized risk score. In some embodiments of the invention, the infection prevention program 110A, 110B may identify multiple risk mitigation protocols that are complimentary; in other words, a group of risk mitigation protocols which can be all be followed simultaneously without violating the tenets or instructions comprising any one of them. The infection prevention program 110A, 110B may, in such cases, calculate a single second risk mitigation protocol for a group of complimentary risk mitigation protocols, representing the risk of the user experiencing the physiological condition while following all or multiple of the group of complimentary risk mitigation protocols.

It may be appreciated that FIGS. 2-3 provide only illustrations of individual implementations and do not imply any limitations with regard to how different embodiments may be implemented. Many modifications to the depicted environments may be made based on design and implementation requirements. For example, according to at least one embodiment of the invention, the infection prevention program 110A, 110B may, by communicating with mobile devices of individuals in proximity to the user, identify individuals or groups of individuals that are following or have been recommended similar or compatible risk mitigation protocols. In some embodiments of the invention, the infection prevention program 110A, 110B may query nearby mobile devices for risk mitigation protocols that the user is following, based for example on prompting the user to enter risk mitigation protocols that the user is following. The infection prevention program 110A, 110B may query a nearby mobile device for risk mitigation protocols that a second user, or user of the nearby mobile device, has been recommended. If the query returns risk mitigation protocols that match those that the user is indicated to be following or has been recommended, the infection prevention program 110A, 110B may flag the second user, and/or individuals recorded as associated with the second user and following the same protocols as the second user, as "safe." Safe users may be indicated or highlighted via graphical elements within the mixed reality environment of the user. In some embodiments of the invention, the infection prevention program 110A, 110B may reassess the individualized risk scores associated with safe individuals based on the risk mitigation protocols that the safe individuals are following, and/or may adjust the dynamic threshold based on the reassessed individualized risk scores and risk mitigation protocols. The infection prevention program 110A, 110B may further select and recommend different risk mitigation protocols in the event of an intruding safe individual, based on the reassessed individualized risk scores. In some embodiments of the invention, the infection prevention program 110A, 110B may analyze behavioral characteristics of the safe users to verify that the safe users are actually following the instructions within the risk mitigation protocols.

Figure 4:
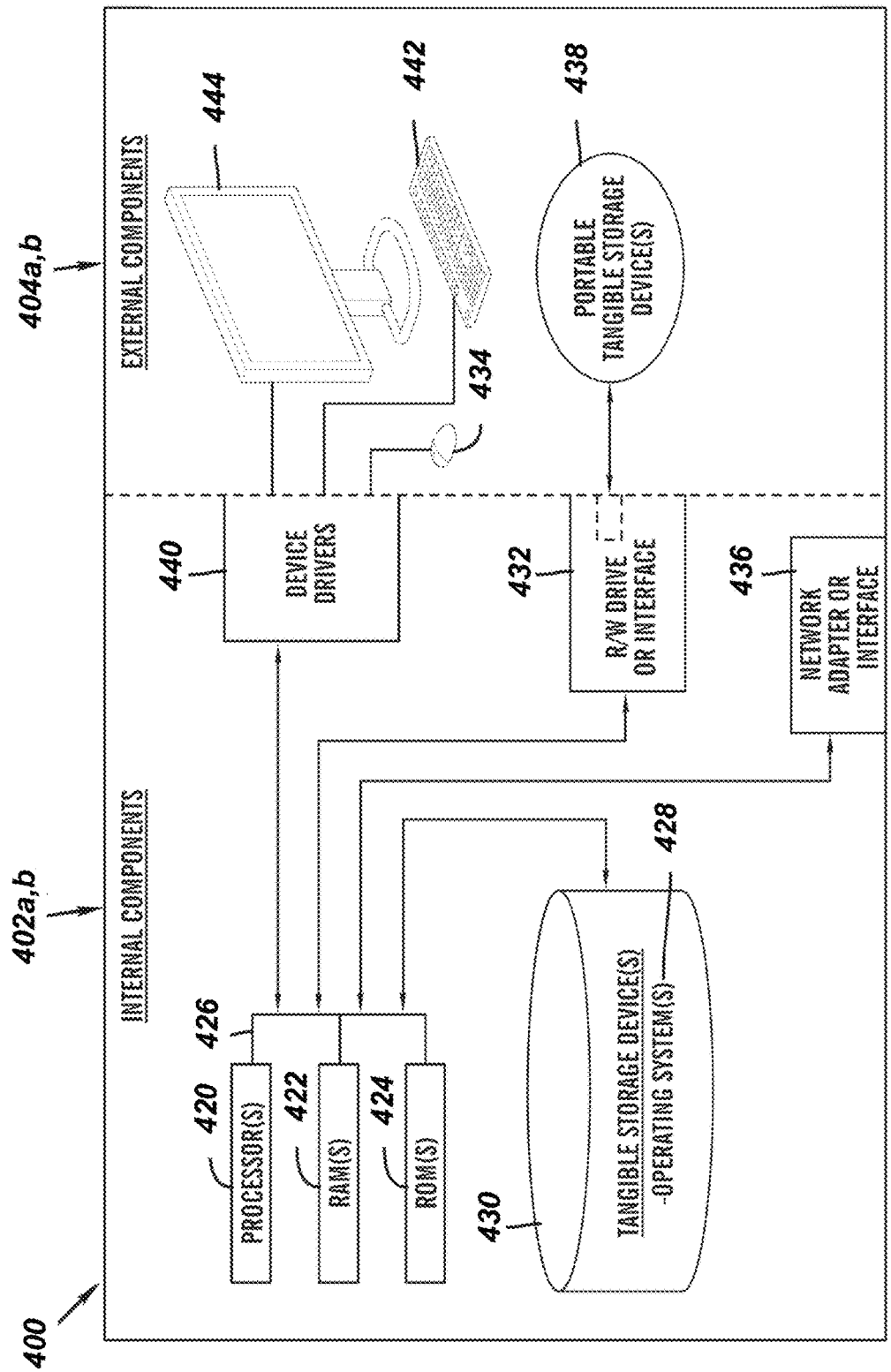
FIG. 4 is a block diagram of internal and external components of computers and servers depicted in FIG. 1 according to at least one embodiment.

FIG. 4 is a block diagram 400 of internal and external components of the client computing device 102 and the server 112 depicted in FIG. 1 in accordance with an embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

The data processing system 402, 404 is representative of any electronic device capable of executing machine-readable program instructions. The data processing system 402, 404 may be representative of a smart phone, a computer system, PDA, or other electronic devices. Examples of computing systems, environments, and/or configurations that may represented by the data processing system 402, 404 include, but are not limited to, personal computer systems, server computer systems, thin clients, thick clients, handheld or laptop devices, multiprocessor systems, microprocessor-based systems, network PCs, minicomputer systems, and distributed cloud computing environments that include any of the above systems or devices.

The client computing device 102 and the server 112 may include respective sets of internal components 402 a,b and external components 404 a,b illustrated in FIG. 4. Each of the sets of internal components 402 include one or more processors 420, one or more computer-readable RAMs 422, and one or more computer-readable ROMs 424 on one or more buses 426, and one or more operating systems 428 and one or more computer-readable tangible storage devices 430. The one or more operating systems 428, the risk protocol database 108 and the infection prevention program 110A in the client computing device 102, and the infection prevention program 110B in the server 112 are stored on one or more of the respective computer-readable tangible storage devices 430 for execution by one or more of the respective processors 420 via one or more of the respective RAMs 422 (which typically include cache memory). In the embodiment illustrated in FIG. 4, each of the computer-readable tangible storage devices 430 is a magnetic disk storage device of an internal hard drive. Alternatively, each of the computer-readable tangible storage devices 430 is a semiconductor storage device such as ROM 424, EPROM, flash memory or any other computer-readable tangible storage device that can store a computer program and digital information.

Each set of internal components 402 a,b also includes a R/W drive or interface 432 to read from and write to one or more portable computer-readable tangible storage devices 438 such as a CD-ROM, DVD, memory stick, magnetic tape, magnetic disk, optical disk or semiconductor storage device. A software program, such as the infection prevention program 110A, 110B, can be stored on one or more of the respective portable computer-readable tangible storage devices 438, read via the respective R/W drive or interface 432, and loaded into the respective hard drive 430.

Each set of internal components 402 a,b also includes network adapters or interfaces 436 such as a TCP/IP adapter cards, wireless Wi-Fi interface cards, or 3G or 4G wireless interface cards or other wired or wireless communication links. The risk protocol database 108 and the infection prevention program 110A in the client computing device 102 and the infection prevention program 110B in the server 112 can be downloaded to the client computing device 102 and the server 112 from an external computer via a network (for example, the Internet, a local area network or other, wide area network) and respective network adapters or interfaces 436. From the network adapters or interfaces 436, the risk protocol database 108 and the infection prevention program 110A in the client computing device 102 and the infection prevention program 110B in the server 112 are loaded into the respective hard drive 430. The network may comprise copper wires, optical fibers, wireless transmission, routers, firewalls, switches, gateway computers and/or edge servers.

Each of the sets of external components 404 a,b can include a computer display monitor 444, a keyboard 442, and a computer mouse 434. External components 404 a,b can also include touch screens, virtual keyboards, touch pads, pointing devices, and other human interface devices. Each of the sets of internal components 402 a,b also includes device drivers 440 to interface to computer display monitor 444, keyboard 442, and computer mouse 434. The device drivers 440, R/W drive or interface 432, and network adapter or interface 436 comprise hardware and software (stored in storage device 430 and/or ROM 424).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
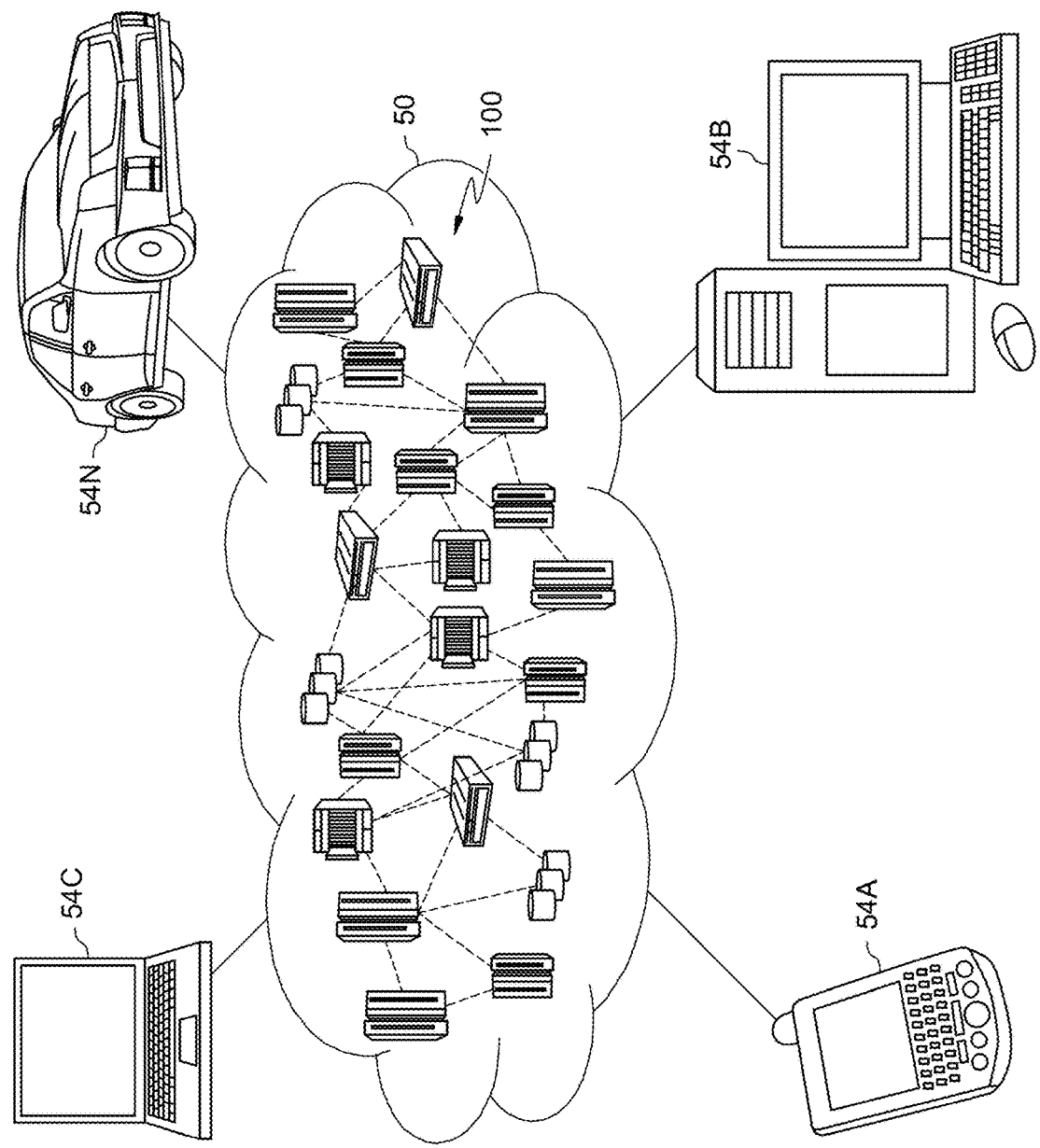
FIG. 5 depicts a cloud computing environment according to an embodiment of the present invention.

Referring now to FIG. 5, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 100 and cloud computing environment 50 can communicate with any type of computerized device over any type of network and/or network addressable connection (e.g., using a web browser).

Figure 6:
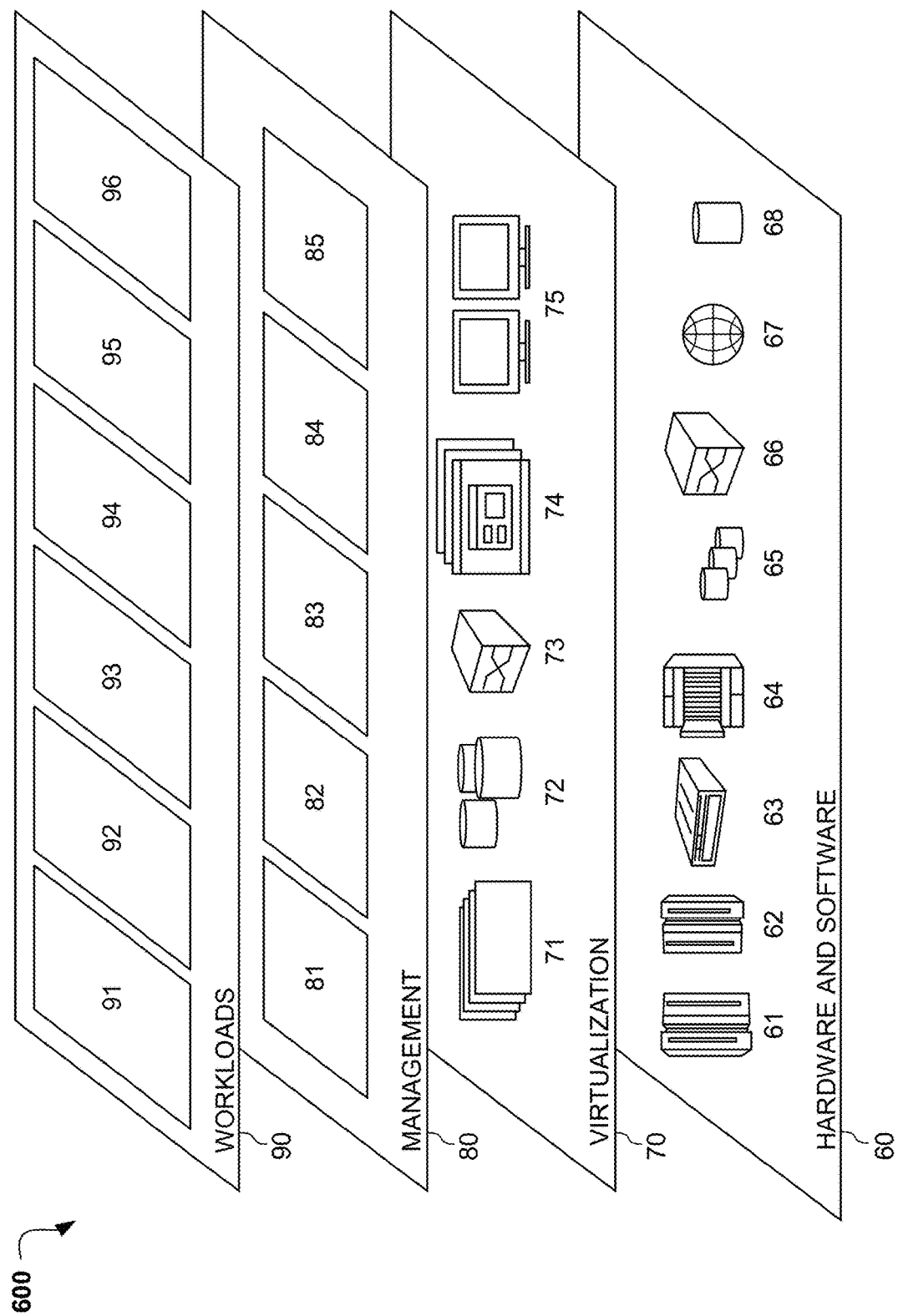
FIG. 6 depicts abstraction model layers according to an embodiment of the present invention.

Referring now to FIG. 6, a set of functional abstraction layers 600 provided by cloud computing environment 50 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and infection prevention 96. The infection prevention 96 may be enabled to detect, dynamically geofence, and warn a user of potential nearby physiological hazards.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A processor-implemented method, the method comprising:
   dynamically monitoring, by one or more sensors integrated into one or more mobile devices on the person of a user, a proximity of the user, wherein the one or more mobile devices comprise at least one mixed-reality device, and wherein the one or more sensors provide a 360-degree arc of camera and/or LIDAR coverage around the user;
   identifying one or more individuals in the proximity of the user based on the monitoring;
   generating, by a processor, one or more dynamic thresholds corresponding to each of the one or more individuals;
   displaying, on the mixed-reality device, at least one of the one or more dynamic thresholds to the user as a circular virtual perimeter centered on an individual of the one or more individuals and which is represented as a graphical overlay within a mixed-reality environment; and
   responsive to a measured distance between an individual of the one or more individuals and the user falling below a dynamic threshold of the one or more dynamic thresholds corresponding with the individual, transmitting, by the processor, an alert to the mixed-reality device.

2. The method of claim 1, further comprising:
   responsive to a distance between an individual of the one or more individuals and the user falling below a dynamic threshold of the one or more dynamic thresholds associated with the individual, transmitting, by the processor, a recommended risk mitigation protocol to the user.

3. The method of claim 1, further comprising:
   responsive to identifying one or more characteristics of an individual of the one or more individuals, updating, by a processor, at least one dynamic threshold of the one or more dynamic thresholds corresponding with the individual.

4. The method of claim 1, wherein the dynamic threshold is based on at least a characteristic of an individual of the one or more individuals, a risk mitigation protocol, and a physiological risk profile of the user.

5. The method of claim 1, further comprising:
   responsive to determining that one or more of the one or more individuals follows a same risk mitigation protocol as the user, adjusting the dynamic threshold distance.

6. The method of claim 1, further comprising:
   responsive to a distance between an individual of the one or more individuals and the user falling below a dynamic threshold of the one or more dynamic thresholds associated with the individual, indicating the individual to the user using one or more mixed reality elements.

7. The method of claim 1, wherein the one or more sensors provide continuous 360-degree sensor coverage of the user in at least two dimensions.

8. A computer system, the computer system comprising:
   one or more mixed-reality devices, one or more sensors integrated into one or more mobile devices on the person of a user, one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
   dynamically monitoring, by one or more sensors integrated into one or more mobile devices on the person of a user, a proximity of the user, wherein the one or more mobile devices comprise at least one mixed-reality device, and wherein the one or more sensors provide a 360-degree arc of camera and/or LIDAR coverage around the user;
   identifying one or more individuals in the proximity of the user based on the monitoring;
   generating, by a processor, one or more dynamic thresholds corresponding to each of the one or more individuals;
   displaying, on the mixed-reality device, at least one of the one or more dynamic thresholds to the user as a circular virtual perimeter centered on an individual of the one or more individuals and which is represented as a graphical overlay within a mixed-reality environment; and
   responsive to a measured distance between an individual of the one or more individuals and the user falling below a dynamic threshold of the one or more dynamic thresholds corresponding with the individual, transmitting, by the processor, an alert to the mixed-reality device.

9. The computer system of claim 8, further comprising: responsive to a distance between an individual of the one or more individuals and the user falling below a dynamic threshold of the one or more dynamic thresholds associated with the individual, transmitting a recommended risk mitigation protocol to the user.

10. The computer system of claim 8, further comprising: responsive to identifying one or more characteristics of an individual of the one or more individuals, updating at least one dynamic threshold of the one or more dynamic thresholds corresponding with the individual.

11. The computer system of claim 8, wherein the dynamic threshold is based on at least a characteristic of an individual of the one or more individuals, a risk mitigation protocol, and a physiological risk profile of the user.

12. The computer system of claim 8, further comprising: responsive to determining that one or more of the one or more individuals follows a same risk mitigation protocol as the user, adjusting the dynamic threshold distance.

13. The computer system of claim 8, further comprising: responsive to a distance between an individual of the one or more individuals and the user falling below a dynamic threshold of the one or more dynamic thresholds associated with the individual, indicating the individual to the user using one or more mixed reality elements.

14. The computer system of claim 8, wherein the one or more sensors provide continuous 360-degree sensor coverage of the user in at least two dimensions.

15. A computer program product, the computer program product comprising:
one or more computer-readable tangible storage medium and program instructions stored on at least one of the one or more tangible storage medium, the program instructions executable by a processor to cause the processor to perform a method comprising:
dynamically monitoring, by one or more sensors integrated into one or more mobile devices on the person of a user, a proximity of the user, wherein the one or more mobile devices comprise at least one mixed-reality device, and wherein the one or more sensors provide a 360-degree arc of camera and/or LIDAR coverage around the user;
identifying one or more individuals in the proximity of the user based on the monitoring;
generating, by a processor, one or more dynamic thresholds corresponding to each of the one or more individuals;
displaying, on the mixed-reality device, at least one of the one or more dynamic thresholds to the user as a circular virtual perimeter centered on an individual of the one or more individuals and which is represented as a graphical overlay within a mixed-reality environment; and
responsive to a measured distance between an individual of the one or more individuals and the user falling below a dynamic threshold of the one or more dynamic thresholds corresponding with the individual, transmitting, by the processor, an alert to the mixed-reality device.

16. The computer program product of claim 15, further comprising:
responsive to a distance between an individual of the one or more individuals and the user falling below a dynamic threshold of the one or more dynamic thresholds associated with the individual, transmitting a recommended risk mitigation protocol to the user.

17. The computer program product of claim 15, further comprising:
responsive to identifying one or more characteristics of an individual of the one or more individuals, updating at least one dynamic threshold of the one or more dynamic thresholds corresponding with the individual.

18. The computer program product of claim 15, wherein the dynamic threshold is based on at least a characteristic of an individual of the one or more individuals, a risk mitigation protocol, and a physiological risk profile of the user.

19. The computer program product of claim 15, further comprising:
responsive to determining that one or more of the one or more individuals follows a same risk mitigation protocol as the user, adjusting the dynamic threshold distance.

20. The computer program product of claim 15, further comprising:
responsive to a distance between an individual of the one or more individuals and the user falling below a dynamic threshold of the one or more dynamic thresholds associated with the individual, indicating the individual to the user using one or more mixed reality elements.

* * * * *